United States Patent
Ducke et al.

(10) Patent No.: US 7,780,717 B2
(45) Date of Patent: Aug. 24, 2010

(54) ROTARY HANDLE FOR CONTROLLED SEQUENTIAL DEPLOYMENT DEVICE

(75) Inventors: Werner Dieter Ducke, Greenwood (AU); David Ernest Hartley, Subiaco (AU); David D. Grewe, West Lafayette, IN (US)

(73) Assignees: MED Institute, Inc., West Lafayette, IN (US); William A. Cook Australia Pty. Ltd., Queensland (AU)

( * ) Notice: Subject to any disclaimer, the term of this patent is extended or adjusted under 35 U.S.C. 154(b) by 522 days.

(21) Appl. No.: 11/789,840

(22) Filed: Apr. 26, 2007

(65) Prior Publication Data

US 2007/0255390 A1 Nov. 1, 2007

Related U.S. Application Data

(60) Provisional application No. 60/795,634, filed on Apr. 27, 2006, provisional application No. 60/795,617, filed on Apr. 27, 2006.

(51) Int. Cl.
*A61F 2/06* (2006.01)
(52) U.S. Cl. ..................................... 623/1.11
(58) Field of Classification Search ................ 623/1.11, 623/1.12; 606/108; 604/107, 108, 109, 165.04, 604/188, 211
See application file for complete search history.

(56) References Cited

U.S. PATENT DOCUMENTS

| | | | | |
|---|---|---|---|---|
| 5,290,310 A | * | 3/1994 | Makower et al. | 606/213 |
| 5,707,376 A | * | 1/1998 | Kavteladze et al. | 623/1.11 |
| 6,203,550 B1 | * | 3/2001 | Olson | 606/108 |
| 6,669,716 B1 | * | 12/2003 | Gilson et al. | 623/1.11 |
| 6,866,669 B2 | * | 3/2005 | Buzzard et al. | 606/108 |
| 2003/0191516 A1 | * | 10/2003 | Weldon et al. | 623/1.12 |
| 2004/0098079 A1 | | 5/2004 | Hartley et al. | |
| 2006/0004433 A1 | * | 1/2006 | Greenberg et al. | 623/1.11 |
| 2007/0168014 A1 | * | 7/2007 | Jimenez et al. | 623/1.12 |

FOREIGN PATENT DOCUMENTS

| WO | WO 2005/070095 | * | 1/2005 |
|---|---|---|---|
| WO | WO 2005070095 A2 | * | 8/2005 |

* cited by examiner

*Primary Examiner*—Todd E Manahan
*Assistant Examiner*—Naquan Ishman
(74) *Attorney, Agent, or Firm*—Richard J. Godlewski

(57) ABSTRACT

A stent graft introducer actuation assembly (1) having a fixed handle (3) and at least one sliding handle (5, 7), the sliding handle or handles telescoping within the fixed handle, and a winch arrangement (9) to retract the sliding handle into the fixed handle. There may be provided arrangements to give a mechanical advantage to the winch arrangement.

5 Claims, 6 Drawing Sheets

ROTARY HANDLE FOR CONTROLLED SEQUENTIAL DEPLOYMENT DEVICE

CROSS-REFERENCE TO RELATED APPLICATIONS

This application is related to and claims priority from U.S. Provisional Patent Application No. 60/795,634 filed Apr. 26, 2006 entitled "Rotary Handle for Controlled Sequential Deployment" the contents of which are incorporated in their entirety herein and for all purposes. This application is related to and claims priority from U.S. Provisional Patent Application Ser. No. 60/795,617 filed Apr. 27, 2006 entitled "Controlled Sequential Deployment" the contents of which are incorporated in their entirety herein and for all purposes.

INCORPORATION BY REFERENCE

The following co-pending patent applications are referred to in the following description:

PCT Patent Publication No. WO 98/53761 entitled "A Prosthesis And A Method And Means Of Deploying A Prosthesis" discloses an introducer for a prosthesis which retains the prosthesis so that each end can be moved independently. These features and other features disclosed in PCT Patent Publication No. WO 98/53761 could be used with the present invention and the disclosure of PCT Patent Publication No. WO 98/53761 is herewith incorporated in its entirety into this specification"

U.S. Provisional Patent Application Ser. No. 60/392,682, filed Jun. 28, 2002, U.S. patent application Ser. No. 10/447,406, filed May 29, 2003, and Published on Dec. 18, 2003, as U.S. Patent Application Publication No. US-2003-0233140-A1 entitled "Trigger Wire System", and PCT Patent Publication No. WO 03/101518 entitled "Trigger Wire System For A Prosthesis Deployment Device" disclose release wire systems for the release of stent grafts retained on introducer devices. This feature and other features disclosed in U.S. Provisional Patent Application Ser. No. 60/392,682, U.S. patent application Ser. No. 10/447,406, and U.S. Patent Application Publication No. US-2003-0233140-A1, and PCT Patent Publication No. WO 03/101518 could be used with the present invention and the disclosure of U.S. Provisional Patent Application Ser. No. 60/392,682, U.S. patent application Ser. No. 10/447,406, and U.S. Patent Application Publication No. US-2003-0233140-A1, and PCT Patent Publication No. WO 03/101518 is herewith incorporated in its entirety into this specification

TECHNICAL FIELD

This invention relates to a controlled sequential deployment device for endovascular stent grafts and more particularly to a method of actuation of such a device.

BACKGROUND OF THE INVENTION

In our earlier patent application, PCT Patent Publication No. WO 98/53761 entitled "A prosthesis and a method deploying a prosthesis" there is disclosed an introducer for a stent graft which retains the stent graft so that each end can be moved independently during the process of endovascular deployment of the stent graft. This device requires that a number of actions be taken in a particular consecutive order to place a stent graft in the required position in the vasculature and then release one end of the stent graft and then another end and if required, between the release of each of the ends, the placement of a branch stent graft from a side arm of the stent graft. These features and other features disclosed in PCT Patent Publication No. WO 98/53761 are incorporated herewith in their entirety into this specification.

It is desirable that the set of sequential actions necessary to release the stent graft at the desired position in the vasculature be undertaken in the required order and that there be less chance for operator error during such a deployment.

In our patent application US Provisional Patent Application Serial No (PA-5858-PRV), a system is disclosed for the controlled sequential deployment of a stent graft into the vasculature of a patient. The device includes at least one telescoping slide which assists in drawing back the sheath from a stent graft and release stent graft retention wires.

It has been found, however, that a stent graft which includes self expanding stents engaging against the inner surface of the sheath, trigger wires retaining the graft onto the pusher as well as the general friction of interacting components can provide significant load. It is the intention of this invention to provide a system to assist with the withdrawing of at least one sliding portion into the handle of a controlled sequential release device.

SUMMARY OF THE INVENTION

In one form therefore, the invention is said to reside in a stent graft introducer actuation assembly, the introducer comprising a pusher, a stent graft releasably retained onto the pusher, a sheath coaxially around the pusher and enclosing the stent graft and a sheath hub to which the sheath is mounted, the actuation assembly comprising a fixed handle and a sliding handle, the sliding handle telescoping within the fixed handle, the sheath hub being retained to the sliding handle and the pusher extending from the fixed handle through the sliding handle, and a winch arrangement to retract the sliding handle into the fixed handle to thereby withdraw the sheath from the stent graft.

Preferably the winch arrangement comprises a ratchet arrangement to allow rotation of the winch arrangement only in a retraction direction.

In a preferred embodiment the winch arrangement comprises a winch drum, a rotation handle for the winch drum and a cable extending from the winch drum to the sliding handle.

The winch drum can be mounted on an axis transverse to the longitudinal extent of the actuation assembly or alternatively the winch drum can be mounted on an axis parallel to the longitudinal extent of the actuation assembly.

Hence, in one embodiment the winch arrangement comprises a winch drum, a rotation handle for the winch drum and a cable extending from the winch drum to the sliding handle, the winch drum and rotation handle rotating on a longitudinal axis parallel to the longitudinal extent of the actuation assembly.

The cable can comprise a band or ribbon of relatively inextensible material or a wire, such as a twisted or braided wire cable.

Preferably the actuation assembly comprises the fixed handle, a release portion and the sliding handle, the release portion telescoping within the fixed handle and the sliding handle telescoping within the release portion.

The actuation assembly can include a first removable stop pin to prevent movement of the sliding handle with respect to the release portion and a second removable stop pin to prevent movement of the release portion with respect to the fixed handle. It may also include a third removable stop pin acting between the fixed handle and the release portion to restrict the distance of retraction of the release portion into the fixed handle until the third stop pin is removed.

The fixed handle can include a first grip and the sliding handle can include a second grip.

In an alternative form the invention comprises a stent graft introducer actuation assembly, the introducer comprising a pusher, a stent graft releasably retained onto the pusher, a sheath coaxially around the pusher and enclosing the stent graft and a sheath hub to which the sheath is mounted, the actuation assembly comprising a fixed handle, a release portion and a sliding handle, the release portion telescoping within the fixed handle and the sliding handle telescoping within the release portion, the sheath hub being retained to the sliding handle and the pusher extending from the fixed handle through the release portion and sliding handle, a winch arrangement to retract the sliding handle and release portion into the fixed handle to thereby withdraw the sheath from the stent graft, a first removable stop pin to prevent movement of the sliding handle with respect to the release portion and a second removable stop pin to prevent movement of the release portion with respect to the fixed handle, a third removable stop pin acting between the fixed handle and the release portion to restrict the distance of retraction of the release portion into the fixed handle until the third removable stop pin is removed, the winch arrangement comprising a winch drum, rotation handle for the winch drum and a cable extending from the winch drum to and affixed to the sliding handle, the winch drum and rotation handle rotating on a longitudinal axis parallel to the longitudinal extent of the actuation assembly and the cable comprising a band or ribbon of relatively inextensible material.

In an alternative form the invention comprises a stent graft introducer actuation assembly comprising a fixed handle and a sliding handle, the sliding handle telescoping within the fixed handle, the sheath hub being retained to the sliding handle and the pusher extending from the fixed handle through the sliding handle, and a winch arrangement to retract the sliding handle into the fixed handle to thereby withdraw the sheath from the stent graft.

In an alternative form the invention comprises a stent graft introducer actuation assembly comprising a fixed handle, a release portion and a sliding handle, the release portion telescoping within the fixed handle and the sliding handle telescoping within the release portion, a winch arrangement to retract the sliding handle and release portion into the fixed handle, a first removable stop pin to prevent movement of the sliding handle with respect to the release portion and a second removable stop pin to prevent movement of the release portion with respect to the fixed handle, a third removable stop pin acting between the fixed handle and the release portion to restrict the distance of retraction of the release portion into the fixed handle until the third removable stop pin is removed, the winch arrangement comprising a winch drum, a rotation handle for the winch drum and a cable extending from the winch drum to and affixed to the sliding handle, the winch drum and rotation handle rotating on a longitudinal axis parallel to the longitudinal extent of the actuation assembly and the cable comprising a band or ribbon of relatively inextensible material.

Throughout this specification the term distal with respect to a portion of the aorta, a deployment device or a prosthesis is the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

This then generally describes the invention but to assist with understanding reference will now be made to the accompanying drawings.

DETAILED DESCRIPTION

Now looking more closely at the drawings and in particular FIGS. 1 to 6 it will be seen that the stent graft introducer actuation assembly 1 comprises generally a fixed handle 3, a first slide or sliding handle 5 and a second slide or release portion 7. On the fixed handle 3 is a rotary handle 9.

Figure 1:
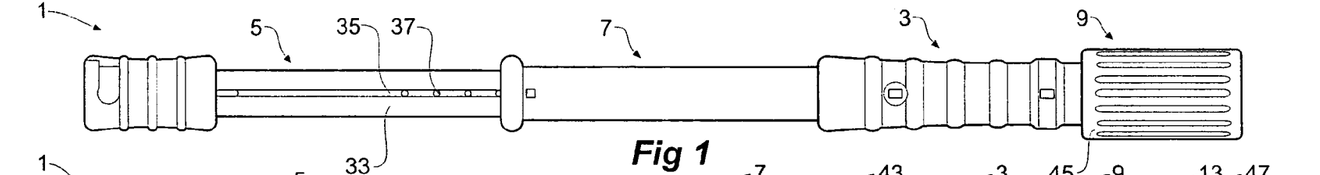
FIG. 1 shows a side view of first embodiment of a stent graft retraction device according to a first embodiment of the present invention.
Figures 2, 3A, 3B, 3C, 4A, 4B, 5A, 5B, 6A, 6B:
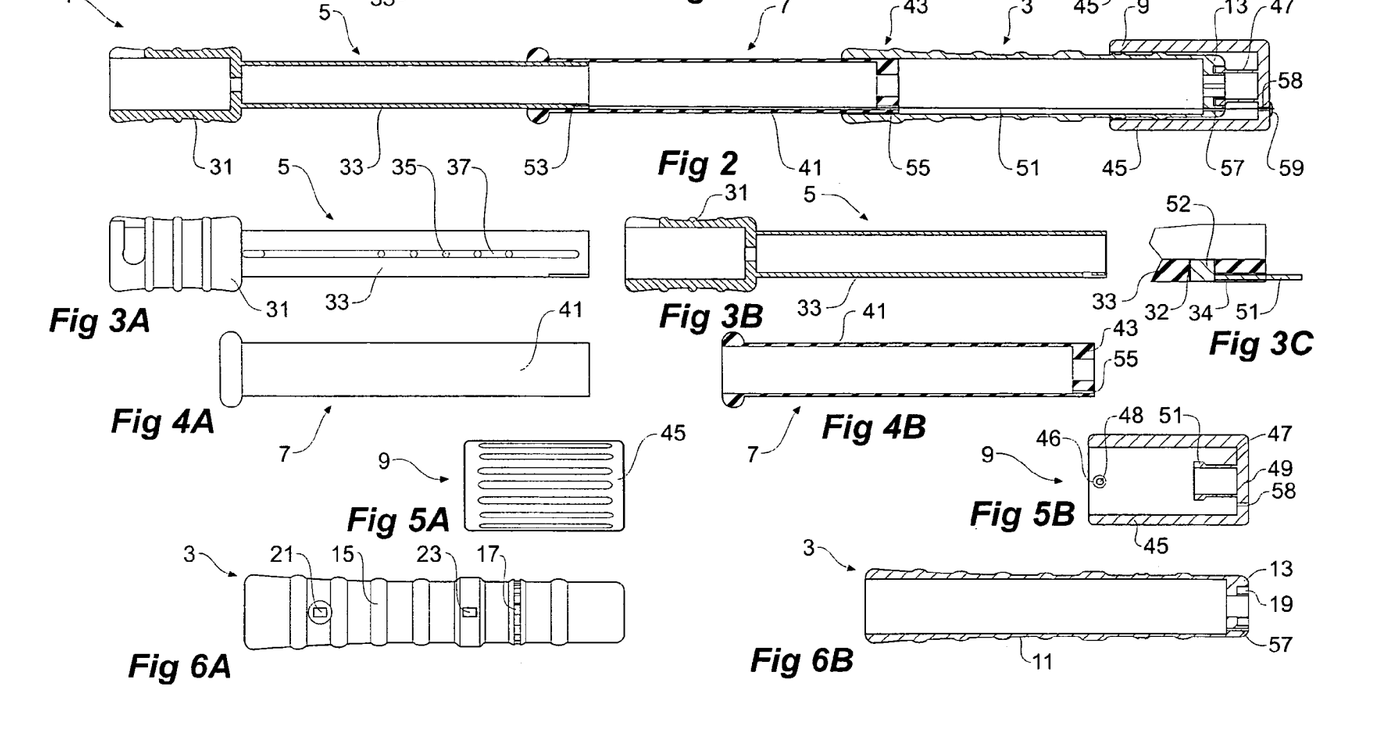
FIG. 2 shows a longitudinal cross-sectional view of the device shown in FIG. 1.
FIGS. 3A, 3B and 3C show a side view and cross-sectional view of a first slide component of the stent graft retraction device of FIG. 1 and a detailed view of the connection of the winch cable to the first slide.
FIGS. 4A and 4B show a top view and cross-sectional view of the second slide component of the stent graft retraction device of FIG. 1.
FIGS. 5A and 5B show a top view and a cross-sectional view of a rotary handle portion of the stent graft stent graft retraction device of FIG. 1.
FIGS. 6A and 6B show a top view and a cross-sectional view of the fixed handle portion of the stent graft retraction device of FIG. 1.

The fixed handle 3 as shown in details in FIGS. 6A and 6B comprises an elongate tubular body 11 with a closed distal end 13. Hand grips 15 are provided on the outside of the fixed handle 3.

A toothed ring 17 is moulded into the outer surface of the fixed handle 3, the use of which will be discussed later. An annular groove 19 in the distal closed end 13 acts as a support for a winch drum which is integral with the rotary handle 9 as will be discussed later. An aperture 21 is provided for a removable second stop pin and aperture 23 is for a third removable stop pin as will be discussed later.

First slide 5 as shown on detail in FIGS. 3A and 3B includes a socket 31 for the hub of a sheath manipulator of a stent graft as will be discussed in relation to FIG. 8. The first slide 5 includes an elongate tubular body 33 with a groove 35 along it into which is engaged a pin (not shown) which prevents relative rotation of the first slide 5 and the second slide 7. Apertures 37 provides an original locking arrangement to prevent movement of the first slide 5 in respect of the second slide 7 until it is required. The selection of which aperture 37 is used depends upon the length of a stent graft deployed using the device of the present invention.

Connection of the cable 51 to the first slide is shown in the detail drawing FIG. 3C. A groove 34 is formed in the wall of the tubular body 33 of the first slide 5 and the groove terminates in a through aperture 32. The cable 51 has a blob of solder or other protrusion 52 formed at its proximal end and the blob 52 is received in the through aperture 32 and the cable 51 lies in the groove 34.

The second slide 7 as shown on detail in FIGS. 4A and 4B includes an elongate tubular body 41 which slides inside the fixed handle 3. The body 41 has a closed distal end 43. The first slide 5 slides within the second slide 7.

The rotary handle 9 as shown on detail in FIGS. 5A and 5B comprises a tubular body 45 which fits over the distal end of the fixed handle 3. Within the tubular body 45 of the rotary handle 9 is a integral winch drum 47 which is formed on the back wall 49 of the rotary handle 9. The winch drum has a bearing protrusion 51 which when mounted to the fixed handle 3 engages in and is supported by the annular groove 19 in the end 13 of the fixed handle 3 as shown in FIG. 6B. A ratchet assembly 46 mounted into the rotary handle 9 has a detent pin 48 which in use engages into the toothed ring 17 (see FIG. 6A) moulded into the outer surface of the fixed handle 3 such that the rotary handle can only be rotated in one direction. The detent pin 48 also assists in holding the rotary handle 9 engaged onto the fixed handle 3.

As can be particularly seen in the cross sectional view, FIG. 2, a cable or inextensible band 51 is mounted at one end to the outer surface of the tubular body 33 of the first slide 5 at position 53 as discussed above in relation to FIG. 3C. The cable extends through an aperture 55 in the rear surface 43 of the second slide 7. The cable then passes through an aperture 57 in the distal end 13 of the fixed handle 3 before extending past the winch drum 47 and then extending through aperture 58 in the rotary handle and being fastened at 59 to the rotary handle 9.

The operation of the winch actuated controlled sequential deployment actuator of one embodiment of the present invention is shown in FIGS. 7A to 7E.

Figure 7A:
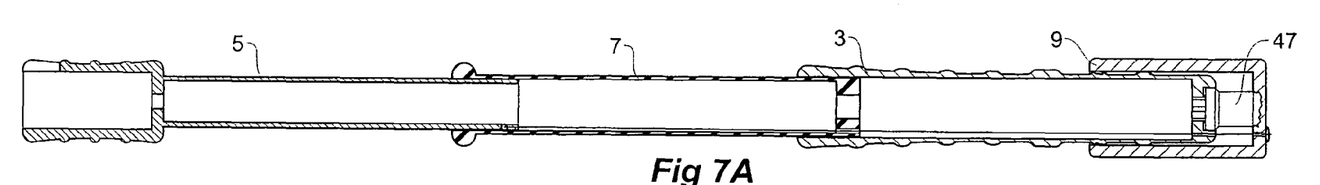
FIGS. 7A to 7E show the various stages of operation of the stent graft introducer actuation assembly of FIG. 1 and FIG. 2.

FIG. 7A shows the same as FIG. 2 except that the winch drum 47 on the rotary handle 9 is shown not in cross-section to more clearly show how it is used. In these views the stent graft deployment device with which the actuation assembly is used is not shown.

Figure 7B:
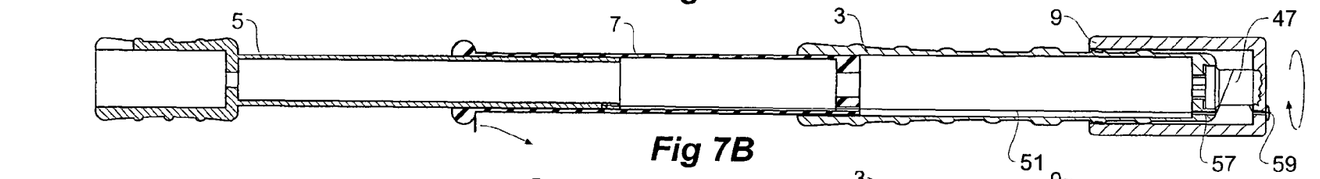

As shown in FIG. 7B the rotary handle 9 has been turned through about one turn and the cable 51 has been drawn around the winch drum 47 because it is fixed at 59 and passes through the aperture 57 in the fixed handle 3. A catch arrangement between the fixed handle 3 and the second slide 7 (not shown) prevents movement of these two items until the first slide 5 has been fully retracted and hence at this stage only the first slide 5 is retracted.

Figure 7C:
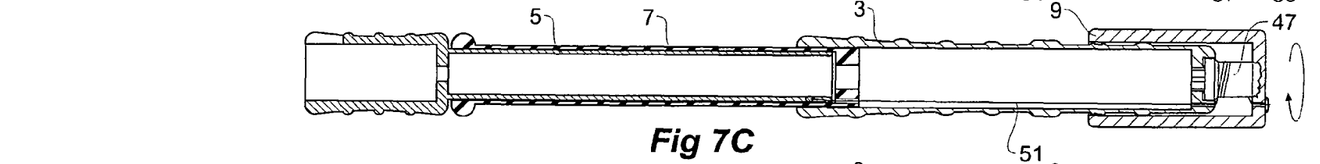

With continued rotation of the rotary handle 9 with respect to the fixed handle 3 as shown in FIG. 7C, more cable 51 has wound on to the drum 47 and the first slide 5 has fully retracted into the second slide 7. At this stage the catch arrangement (not shown) is released so that the second slide can move in respect to the fixed handle 3.

Figure 7D:
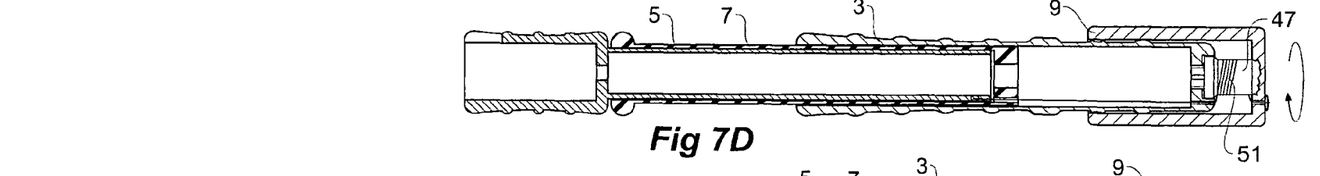
Figure 7E:
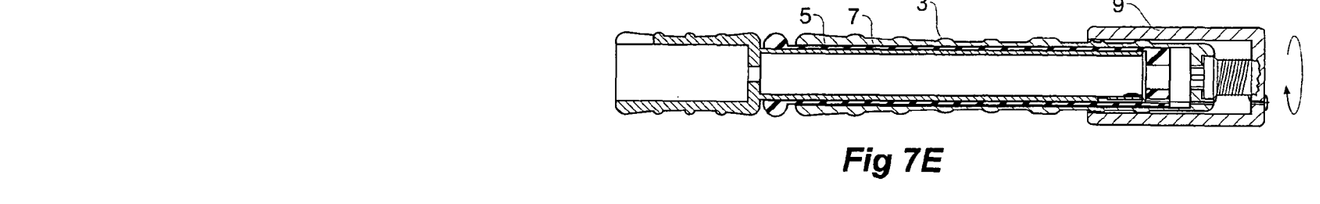

Also as shown in FIGS. 7D and 7E, continued rotation of the rotary handle 9 with respect to the fixed handle 3 winds more cable 51 onto the drum 47 and the first and the second slides 5 and 7 respectively move into the fixed handle 3.

It will be seen therefore that by holding the fixed handle 3 stationary and rotating the rotary handle 9 the cable 51 is caused to wind onto the winch drum 47 and this causes the first and second slides to be withdrawn into the fixed handle 3.

Figure 8:
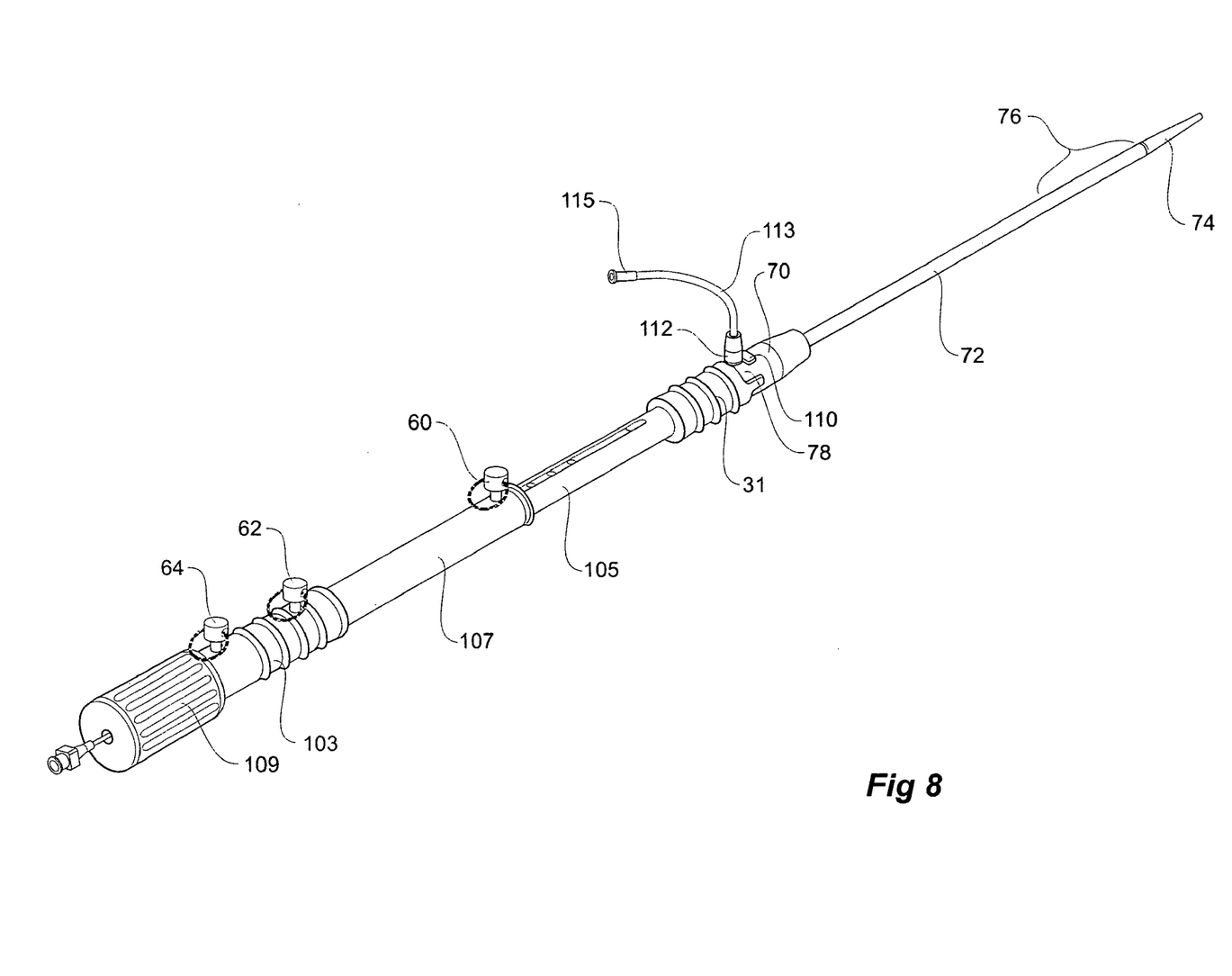
FIG. 8 shows a perspective view of a stent graft introducer and actuation handle assembly according to the embodiment of the invention shown in FIG. 1.

FIG. 8 shows the assembly of a controlled sequential actuation device according to the embodiment shown in FIGS. 1 to 6 with a stent graft deployment device mounted into it. The actuation device includes a fixed handle 103 with a first slide 105, a second slide 107 and a rotary handle 109. A first removable stop pin 60 prevents relative movement of the first slide 105 in respect to the second slide 107 until it is removed. A second removable stop pin 62 prevents relative movement of the second slide 107 into the fixed handle 103. A third removable stop pin 64 prevents complete retraction of the second slide 107 into the fixed handle 103 until it is removed.

The stent graft introducer mounted onto the actuation assembly includes a hub assembly 70, a sheath 72 mounted onto the hub and a nose cone dilator 74. The stent graft to be introduced is retained in the region 76 underneath the sheath 72. A main pusher catheter (not shown) of the stent graft introducer extends from the fixed handle 103 to distal of the stent graft in the region 76 just distal of the nose cone dilator 74. The hub 70 of the sheath manipulator is mounted into the socket 31 by means of a bayonet clip arrangement 78.

Rotation of the rotary handle 109 in respect of the fixed handle 103 causes the sheath 72 to be retracted distally from the nose cone dilator to expose and release the stent graft 76.

Figure 9A:
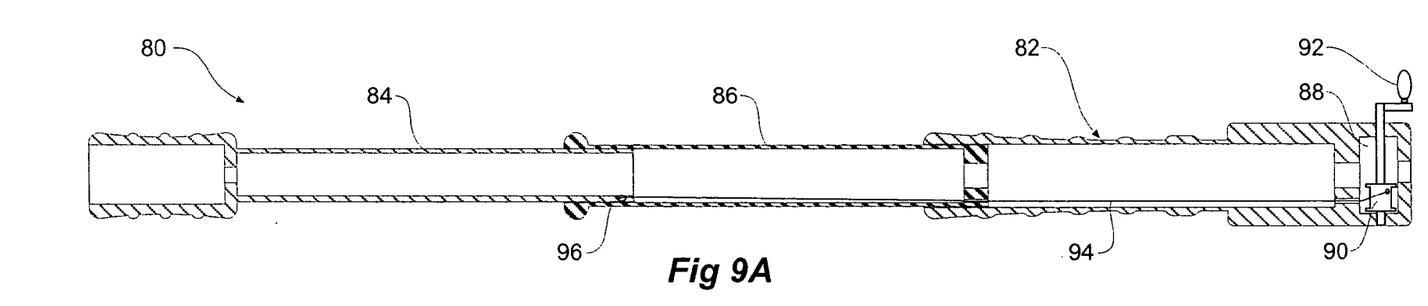
FIGS. 9A to 9C show the various stages of operation of an alternative embodiment of a stent graft introducer actuation assembly according to the present invention.
Figure 9B:
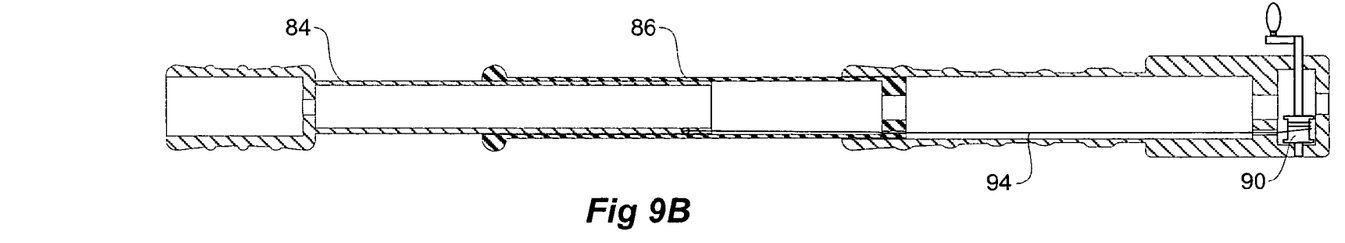
Figure 9C:
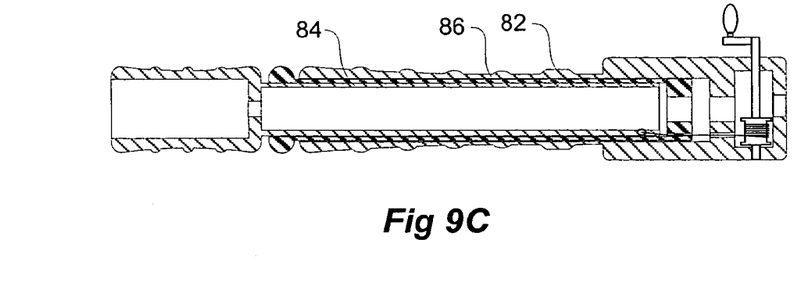

FIGS. 9A to 9C show in cross sectional view an alternative embodiment of actuation assembly for stent graft introducer. In these views the stent graft deployment device with which the actuation assembly is used is not shown.

In this embodiment the actuation assembly 80 includes a fixed handle 82, a first slide 84 and a second slide 86. In the fixed handle 82 there is an interior recesses 88 into which is mounted a winch drum 90 actuated by handle 92. A cable 94 is mounted to the winch drum 90 and extends forward to be mounted at 96 in the first slide 84.

In a similar manner to that explained in relation to FIG. 7, rotation of the winch handle causes the cable 94 to be wound onto the winch drum 90 so that the first slide 84 is retracted into the second slide 86 and then as shown in FIG. 9B the first and second slides are retracted into the fixed handle 82 until both slides are fully retracted as shown in FIG. 9C.

Figure 10:
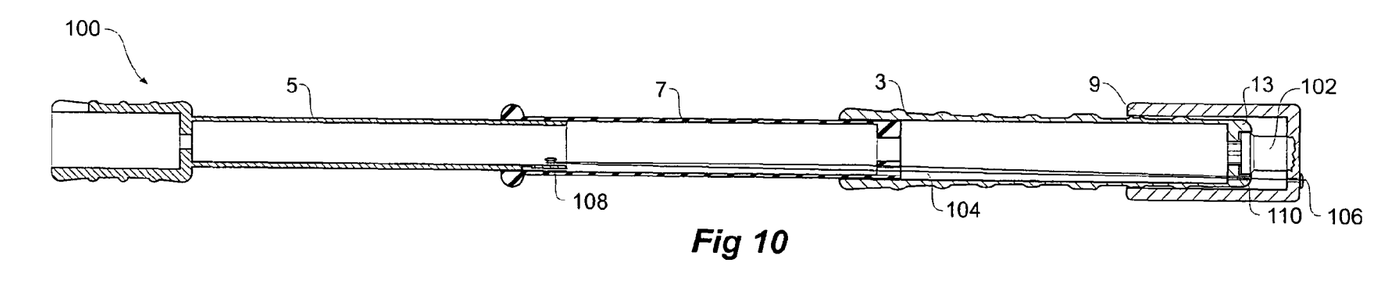
FIG. 10 show the an alternative embodiment of a stent graft introducer actuation assembly according to the present invention.

FIG. 10 shows an alternative embodiment of a stent graft introducer actuation assembly according to the present invention. In this embodiment the same reference numerals as used in relation to FIGS. 1 to 6 are used for corresponding items.

The stent graft introducer actuation assembly 100 of this embodiment comprises generally a fixed handle 3, a first slide 5 and a second slide 7. On the fixed handle 3 is a rotary handle 9. To give additional mechanical advantage to the winch arrangement 102 on the rotary handle 9 the cable 104 extends from its fixing point 106 on the rotary handle to a boss or pulley on the first slide 5 and then back to a fixing 110 on the end piece 13 of the fixed handle 3. Rotation of the rotary handle 9 will give an increased mechanical advantage to retraction of the slides.

Figure 11:
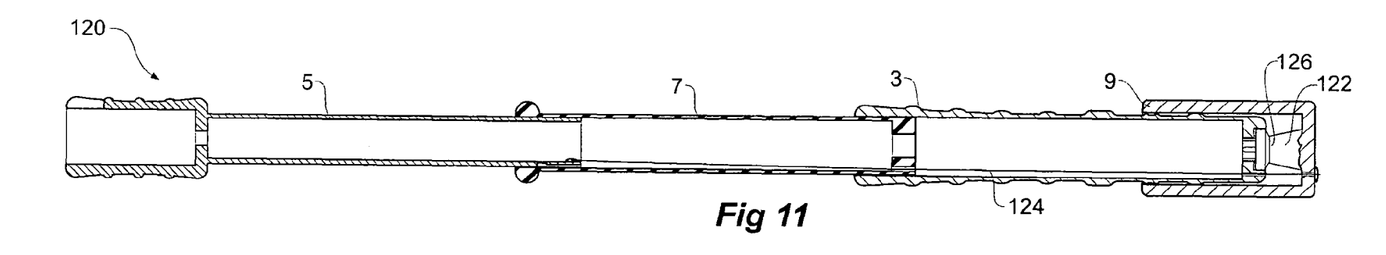
FIGS. 11 and 11A show a still further alternative embodiment of a stent graft introducer actuation assembly according to the present invention and its method of operation.
Figure 11A:
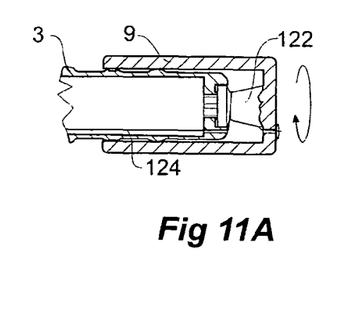

FIGS. 11 and 11A show a still further alternative embodiment of a stent graft introducer actuation assembly according to the present invention and its method of operation. In this embodiment the same reference numerals as used in relation to FIGS. 1 to 6 are used for corresponding items.

The stent graft introducer actuation assembly 120 of this embodiment comprises generally a fixed handle 3, a first slide 5 and a second slide 7. On the fixed handle 3 is a rotary handle 9. To give additional mechanical advantage to the winch arrangement 102 on the rotary handle 9 the winch drum 122 is tapered to give a reduced diameter 126 where the cable 124 first winds onto the winch drum. This means that additional turns are necessary to retract the slides early on in retraction of the first slide into the second slide which will give an increased mechanical advantage to the retraction where it is needed most due to greater friction.

Figure 12:
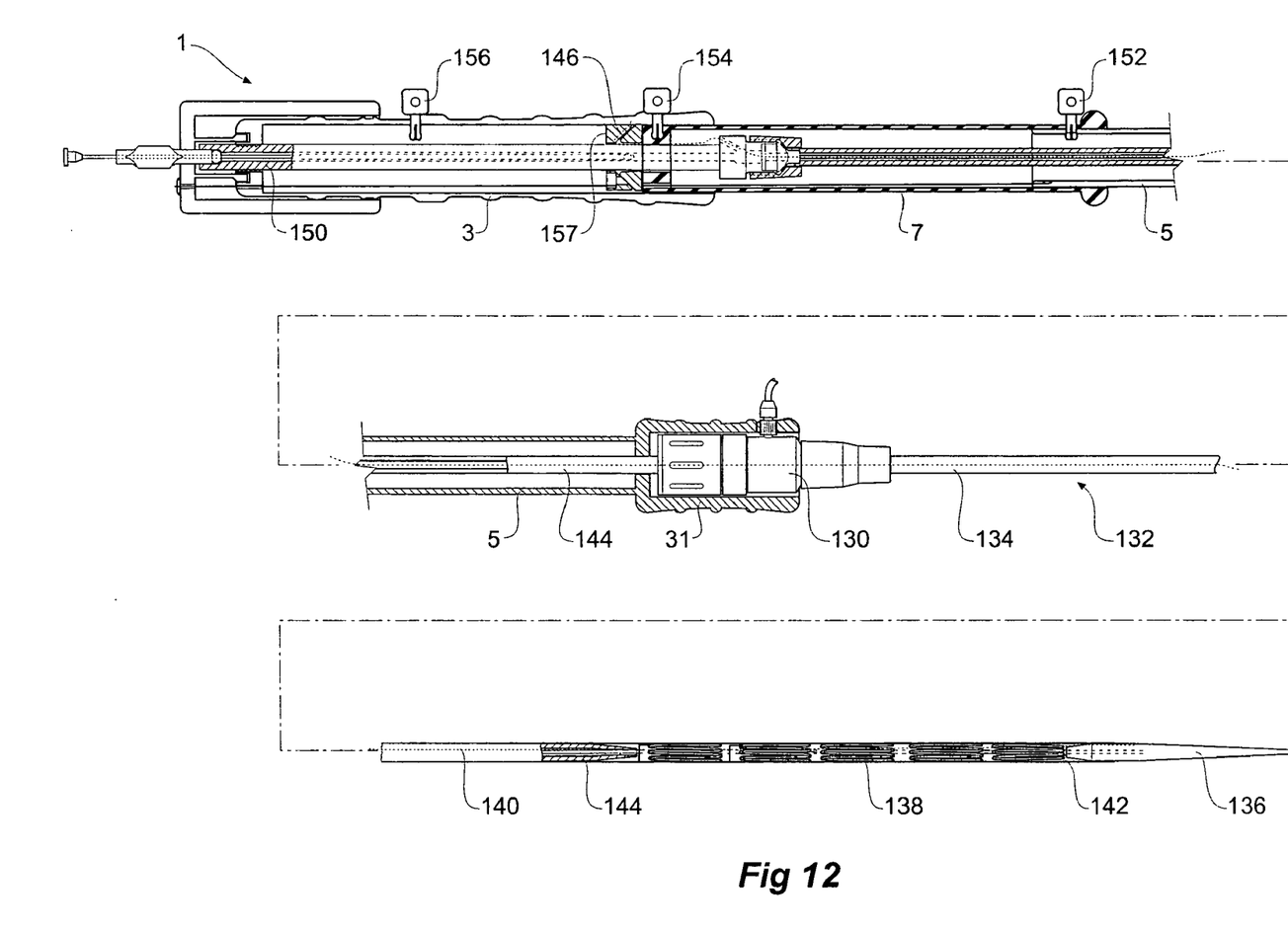
FIG. 12 shows a shows a longitudinal cross-sectional view of the embodiment of the actuation assembly shown in FIGS. 1 to 6 with a stent graft introducer carried in it.

FIG. 12 shows a longitudinal cross-sectional view of the embodiment of the actuation assembly shown in FIGS. 1 to 6 with a stent graft introducer carried in it.

In this embodiment, the actuation assembly 1 comprises a handle portion 3, a first slide 5 and a second slide 7. The first slide 5 has a hub retention socket 31 and into this is received the hub 130 of a stent graft introduction assembly 132. A sheath 134 is mounted to the hub 130 and extends forward to a nose cone dilator 136. Just distal of the nose cone dilator and within the sleeve 134 a stent graft 138 is retained. A trigger wire 140 or a set of trigger wires engages with the exposed stent 142 at the proximal end of the stent graft 138 and retains the proximal end of the stent graft to the stent graft introduction assembly 132. The trigger wire or wires extend distally through a lumen of the pusher catheter 144 to a trigger wire clamp 146 at the distal end of the second slide 7.

A method of retention of the proximal end of a stent graft onto a introducer is disclosed in PCT Publication WO03/101518 entitled "Trigger Wire System for a Prosthesis Deployment Device". This feature and other features disclosed in PCT Publication WO03/101518 could be used with the present invention and the disclosure of PCT Publication WO03/101518 is herewith incorporated in its entirety into this specification.

The hub 130 is retained in the hub socket 31 on the first slide 5 by means of a bayonet lock arrangement as can be see particularly in FIG. 8.

The pusher catheter 144 extends back through the hub 130 to a mounting position 150 within the handle portion 3. The first slide 5 slides within the second slide 7 and a first removable stop pin 152 prevents relative movement of the first slide within the second slide until the locking pin 152 has been removed. The second slide 7 includes the trigger wire clamp 146 at the distal end thereof and a second removable stop pin 154.

A third removable stop pin 156 provides an intermediate stop positions during withdrawal of the sheath 134 from the stent graft 138.

In a first stage of operation of the stent graft introducer actuation assembly according to this embodiment the first removable stop pin 152 is withdrawn so that the first slide 5 can slide within the second slide 7. As the hub 130 is connected to the first slide 5, the hub and therefore the sheath 134 is withdrawn from the nose cone dilator 136 so that the stent graft 138 is partially exposed. At this stage, the exposed stent 142 at the proximal end of the stent graft 138 is still retained just distal of the nose cone dilator 136.

In the next stage the first slide 5 continues to slide back inside the second slide 7 until the distal end of the first slide 5 is fully retracted into the second slide 7. The second removable stop pin 154 can then be removed which enables the second slide 7 and first slide 5 to be able to slide into the handle portion 3.

At this stage, more of the stent graft 138 is exposed but the exposed stent 142 at the proximal end of the stent graft 138 is still retained just distal of the nose cone dilator 136.

Continued movement of the first slide 5 along with the second slide 7 within the handle portion 3 can occur until the distal end 157 of the second slide 7 engages third removable stop pin 156. During this stage, because the distal end of the trigger wire or wires 140 are clamped by the trigger wire clamp 146 on the distal end of the second slide 7, movement of the second slide 7 pulls the trigger wire 140 from its retention arrangement at the proximal end of the stent graft 138 so the proximal end of the stent graft is freed. At the same time, the sheath 134 has been withdrawn so that the distal end of the main body of the stent graft 138 is still retained within the sheath.

At this stage, a side arm can be deployed such as in relation to deployment about the aortic bifurcation by access from the contra-lateral iliac artery to engage an extension arm into the side arm. Our earlier PCT Patent Publication No. WO 98/53761 discussed above showed how such a deployment can be done.

The third removable stop pin 156 can then be removed and the first and second slides continued in their movement back into the handle portion 3. Completion of the movement of the first and second slides 5 and 7 into the handle portion 3 ensures that the sheath 134 is completely withdrawn from the stent graft 138 and the stent graft 138 is released.

The hub 130 can then be released from the hub socket 31 on the first slide 5 so that the pusher 144 and nose cone dilator 136 can be withdrawn through the sleeve 134 along with the actuation assembly, leaving the hub and sheath in place. Subsequent deployment operations can be made through the sheath 134 and hub 130 as required.

It will be seen by this invention an arrangement is provided by which considerable mechanical advantage can be provided to retract the sheath of a stent graft introducer to assist with overcoming friction between the stent graft and a enclosing sheath.

What is claimed is:

1. An actuation assembly in combination with a stent graft introducer and a stent graft, the introducer comprising a pusher, the stent graft being releasably retained onto the pusher, a sheath coaxially around the pusher and enclosing the stent graft and a sheath hub to which the sheath is mounted, the actuation assembly comprising a fixed handle, a release portion and a sliding handle, the release portion telescoping within the fixed handle and the sliding handle telescoping within the release portion, the sheath hub being retained to the sliding handle and the pusher extending from the fixed handle through the release portion and the sliding handle, a winch arrangement to retract the sliding handle and release portion into the fixed handle to thereby withdraw the sheath from the stent graft, the winch arrangement being associated with the fixed handle, the fixed handle comprising a distal end remote from the stent graft introducer, the winch arrangement comprising a rotary handle at the distal end of the fixed handle, a winch drum within the rotary handle, and a cable extending from the winch drum through the fixed handle and the release portion to and affixed to the sliding handle, the winch drum and rotary handle rotating on a longitudinal axis parallel to the longitudinal extent of the actuation assembly and the cable comprising a band or ribbon of relatively inextensible material.

2. An actuation assembly as in claim 1 wherein the winch arrangement comprises a ratchet arrangement engaging against the fixed handle to allow rotation of the winch arrangement only in a retraction direction.

3. An actuation assembly as in claim 1 wherein the fixed handle includes a first grip and the sliding handle includes a second grip.

4. An actuation assembly as in claim 1 comprising a first removable stop pin to prevent movement of the sliding handle with respect to the release portion and a second removable stop pin to prevent movement of the release portion with respect to the fixed handle.

5. An actuation assembly as in claim 4 comprising a third removable stop pin acting between the fixed handle and the release portion to restrict the distance of retraction of the release portion into the fixed handle until the third removable stop pin is removed.

* * * * *